(12) United States Patent
Colvin et al.

(10) Patent No.: US 7,706,892 B2
(45) Date of Patent: Apr. 27, 2010

(54) IMPLANTABLE MICROSTIMULATOR WITH PLASTIC HOUSING AND METHODS OF MANUFACTURE AND USE

(75) Inventors: Michael Steven Colvin, Malibu, CA (US); Tom Xiaohai He, Simi Valley, CA (US); Matt Isaac Haller, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 717 days.

(21) Appl. No.: 11/040,209

(22) Filed: Jan. 20, 2005

(65) Prior Publication Data

US 2006/0161204 A1 Jul. 20, 2006

(51) Int. Cl.
*A61B 5/042* (2006.01)
*A61B 1/05* (2006.01)

(52) U.S. Cl. ...................................... 607/116; 600/373

(58) Field of Classification Search ......... 600/373–381; 607/116, 118
See application file for complete search history.

(56) References Cited

U.S. PATENT DOCUMENTS

| | | | | |
|---|---|---|---|---|
| 3,555,171 | A * | 1/1971 | Larson | 174/138 F |
| 3,718,142 | A | 2/1973 | Mulier | |
| 3,720,209 | A * | 3/1973 | Bolduc | 600/395 |
| 3,835,432 | A * | 9/1974 | Caione | 337/247 |
| 5,193,539 | A | 3/1993 | Schulman et al. | |
| 5,193,540 | A | 3/1993 | Schulman et al. | |
| 5,312,439 | A | 5/1994 | Loeb | |
| RE34,696 | E * | 8/1994 | Ohdate | 257/689 |
| 5,405,367 | A | 4/1995 | Schulman et al. | |
| 6,051,017 | A | 4/2000 | Loeb et al. | |
| 6,185,452 | B1 | 2/2001 | Schulman et al. | |
| 6,214,032 | B1 | 4/2001 | Loeb et al. | |
| 6,297,943 | B1 * | 10/2001 | Carson | 361/500 |
| 6,809,701 | B2 | 10/2004 | Amundson et al. | |
| 6,845,267 | B2 * | 1/2005 | Harrison et al. | 607/3 |
| 6,947,782 | B2 * | 9/2005 | Schulman et al. | 600/373 |
| 6,963,770 | B2 * | 11/2005 | Scarantino et al. | 600/436 |
| 7,174,218 | B1 * | 2/2007 | Kuzma | 607/116 |
| 7,239,921 | B2 | 7/2007 | Canfield et al. | |
| 2002/0193859 | A1 * | 12/2002 | Schulman et al. | 607/116 |
| 2003/0083728 | A1 * | 5/2003 | Greatbatch et al. | 607/122 |
| 2003/0191504 | A1 * | 10/2003 | Meadows et al. | 607/33 |
| 2004/0010296 | A1 | 1/2004 | Swanson et al. | |
| 2004/0059392 | A1 | 3/2004 | Parramon et al. | |

FOREIGN PATENT DOCUMENTS

| | | |
|---|---|---|
| WO | 98/37926 | 9/1998 |
| WO | 98/43700 | 10/1998 |
| WO | 98/43701 | 10/1998 |

* cited by examiner

*Primary Examiner*—Carl H. Layno
*Assistant Examiner*—Tammie K Heller
(74) *Attorney, Agent, or Firm*—Darby & Darby P.C.; Patrick R. Turner

(57) ABSTRACT

An implantable microstimulator includes a plastic housing having a first end and a second end; an electronic subassembly disposed within the housing; a first electrode disposed at the first end of the plastic housing and in electrical communication with the electronic subassembly; and a second electrode disposed at the second end of the plastic housing and in electrical communication with the electronic subassembly. The plastic housing, first electrode, and second electrode form a hermetically sealed structure around the electronic subassembly.

19 Claims, 5 Drawing Sheets

IMPLANTABLE MICROSTIMULATOR WITH PLASTIC HOUSING AND METHODS OF MANUFACTURE AND USE

FIELD

The invention is directed to implantable microstimulators with exposed electrodes and methods of using the devices. In addition, the invention is directed to implantable microstimulators with exposed electrodes and a plastic housing and methods of using the devices.

BACKGROUND

Implantable microstimulators have been developed to provide therapy for a variety of disorders, as well as other treatments. For example, implantable microstimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. It is preferable that the electronic circuitry and power source be held within the housing in a hermetically-sealed environment for the protection of the user and the protection of the circuitry and power source. Once implanted, it is often preferable that the microstimulator can be controlled and/or that the electrical source can be charged without removing the microstimulator from the implanted environment.

BRIEF SUMMARY

One embodiment is an implantable microstimulator that includes a plastic housing having a first end and a second end; an electronic subassembly disposed within the housing; a first electrode disposed at the first end of the plastic housing and in electrical communication with the electronic subassembly; and a second electrode disposed at the second end of the plastic housing and in electrical communication with the electronic subassembly. The plastic housing, first electrode, and second electrode form a hermetically sealed structure around the electronic subassembly.

Another embodiment is a microstimulation system that includes the implantable microstimulator described above and an external control unit. The external control unit is configured and arranged to communicate with the electronic subassembly of the microstimulator to provide signals to the implantable microstimulator.

Yet another embodiment is a method of treating body tissue. The microstimulator described above is implanted into a body. The microstimulator operates to stimulate the body tissue using the first and second electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
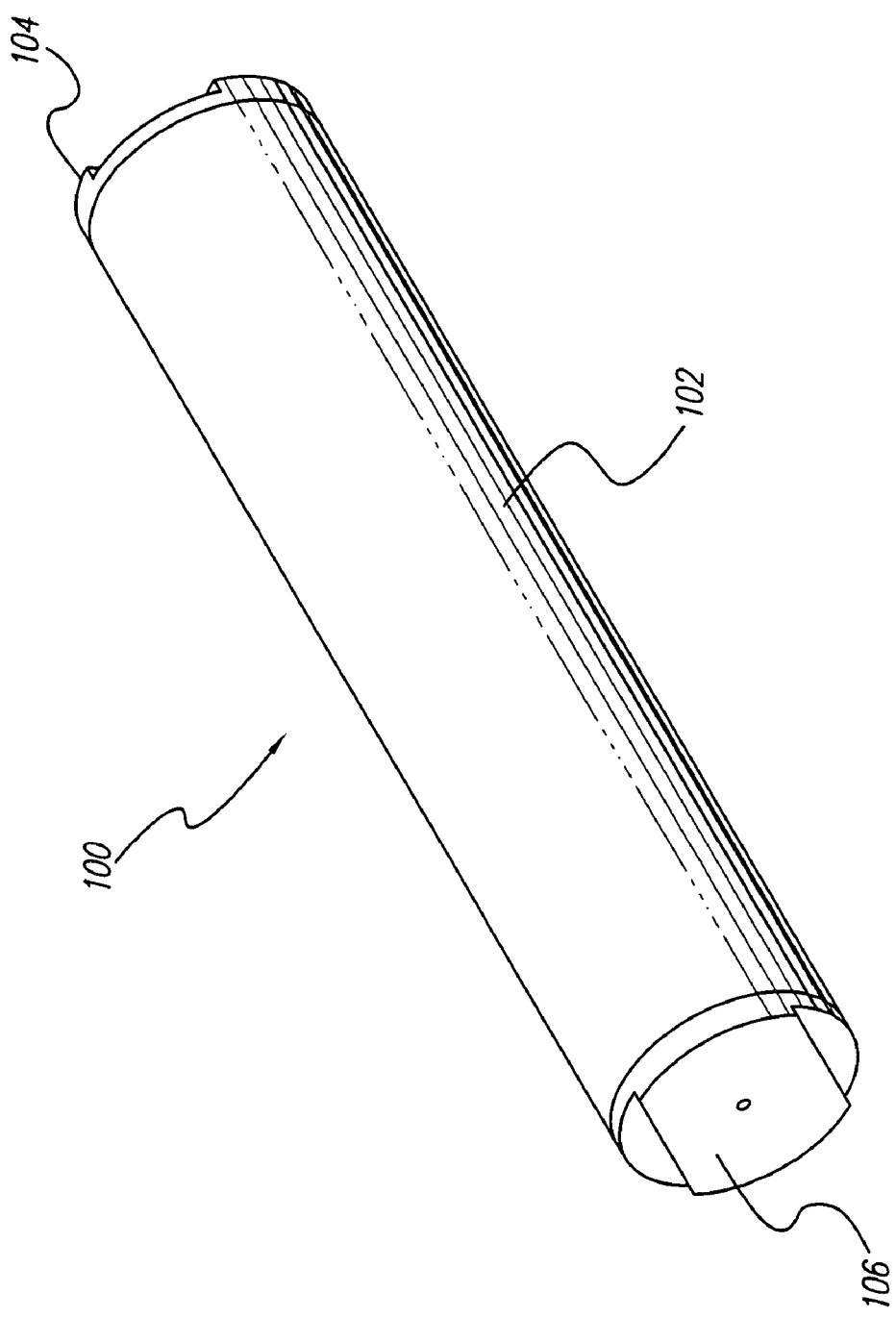
FIG. 1 is a schematic exterior perspective view of one embodiment of a microstimulator, according to the invention.

The present invention is directed to the area of implantable microstimulators with exposed electrodes and methods of using the devices. In addition, the invention is directed to implantable microstimulators with exposed electrodes and a plastic housing and methods of using the devices.

Previously, implantable microstimulators have been made using housings of metal (for example, titanium) and ceramic components. Examples of such microstimulators are found in U.S. Pat. Nos. 5,139,539; 5,239,540; 5,312,439; 6,051,017; and 6,609,032; U.S. Patent Application Publication No. 2004/059392; and PCT Patent Applications Publication Nos. 98/37926; 98/43700; and 98/43701, all of which are incorporated herein by reference. The manufacture of such microstimulators typically includes brazing steps to couple the metal and ceramic components together to form a hermetically-sealed device.

An implantable microstimulator can be formed using a plastic housing with electrodes attached to the plastic housing. The plastic housing and electrodes can form a hermetically-sealed device. In at least some embodiments, the implantable microstimulator with plastic housing can be easier or less costly to manufacture, or there can be a reduction in the time, manpower, or skill used to manufacture the device, when compared to earlier implantable microstimulators. In particular, the implantable microstimulator with plastic housing typically does not involve brazing operations. In addition, the plastic housing may be more permeable to RF signals than metal or ceramic. These RF signals can be used to charge a battery in the housing or to provide data or instructions to a processor disposed in the housing.

FIGS. 1 to 4 illustrate one embodiment of an implantable microstimulator 100. The implantable microstimulator 100 includes a plastic housing 102, a first electrode 104, a second electrode 106, a power source 120, an electronics subassembly 122, and an optional antenna 124. Other embodiments of an implantable microstimulator may include more or fewer components.

The plastic housing 102 can be formed of a plastic material that resists the transport of moisture into the interior of the housing and is sufficiently sturdy to protect the components on the interior of the housing from damage under expected implantation and usage conditions. Preferably, the material of the plastic housing is a hydrophobic polymer material. The plastic material of the housing can be homopolymer, a copolymer formed using two or more different monomeric units, or a mixture of polymers or other materials. Examples of suitable polymer materials include polyolefins, polypropylene homopolymers and copolymers, TEFLON™, and polyetheretherketone (PEEK). The plastic housing may also include additives such as, for example, fillers, plasticizers, antioxidants, colorants, and the like.

The thickness of the walls of the plastic housing may also impact the moisture permeability of the plastic housing. A minimum thickness needed to achieve a particular degree of resistance to moisture transport will often depend on the material selected for the housing, as well as any additives. In general, however, the thickness of the walls of the plastic housing is at least 100 μm and typically ranges from 50 to 10,000 μm.

The plastic housing can have any shape including, for example, cylindrical, conical, parallelepiped, cubic, and the like. In at least some embodiments, a cylindrical shape is preferred. The lateral cross-sectional dimensions can be the same or can vary along the length of plastic housing. In one embodiment, the plastic housing has a cylindrical shape with a uniform diameter along the length of the plastic housing. The uniform diameter can be, for example, no greater then 5 mm, no greater than 4 mm, no greater than 3.3 mm, or no greater than 3 mm. This uniform diameter can be in the range of from, for example, 1 to 5 mm. In another embodiment, the plastic housing is a cylinder that is wider at the ends and narrower in the middle or the plastic housing is a cylinder that is wider in the middle and narrower at the ends.

Optionally, the plastic housing can be covered, in full or in part, with a coating. The coating can be provided to improve or alter one or more properties of the plastic housing including, for example, biocompatibility, hydrophobicity, moisture permeability, leaching of material into or out of the plastic housing, and the like. The optional coating can be a polymer material, inorganic material, or organic material. As an example, the plastic housing may be coated with an inorganic material, such as, for example, silicon dioxide, silicon nitride, titanium dioxide, or the like, to reduce moisture permeability. As another example, a silicone coating may be used in to improve biocompatibility. In yet another example, a coating can be applied which contains a compound, such as, for example, a drug, prodrug, hormone, or other bioactive molecule, that can be released over time when the microstimulator is implanted. (In another embodiment, the plastic housing itself may include such a compound to be released over time after implantation.) In some embodiments, the coating includes two or more layers of the same or different materials. For example, alternating layers of inorganic materials can be deposited as a coating to improve resistance to moisture transport through the plastic housing.

The formation of the coating can be accomplished using any method including, for example, dip-coating, sputtering, reactive sputtering, physical or chemical vapor deposition, spray coating, and the like. The coating can be applied before the other microstimulator components have been assembled with the plastic housing or at any other point in the microstimulator manufacturing process including applying the coating after the microstimulator has been completely assembled. Typically, the coating is non-conductive.

The electrodes 104, 106 typically form the anode and cathode of the microstimulator. These electrodes can be formed of the same or different conductive materials. Preferably, the electrodes are formed of materials that do not substantially corrode under the operating conditions and in the operating environment for the expected lifetime of the microstimulator. Examples of suitable materials include metals, alloys and other conductive materials such as, for example, titanium, iridium, platinum, platinum iridium, stainless steel, and the like.

The electrodes 104, 106 can be formed entirely of a single conductive material, such as a metal or alloy, or one or both of the electrodes can be formed using a combination of conductive materials such as, for example, a conductive coating over a bulk metallic electrode. In other embodiments, one or both of the electrodes 104, 106 can be formed from a polymeric material that is at least partially, or fully, coated with a conductive coating, such as a metal, alloy, or conductive oxide (e.g., iridium oxide) coating.

Each of the electrodes can be a solid body that fits into one end of the plastic housing. The electrode can be coupled to the battery and electronic subassembly by attaching a lead to an interior surface of the electrode.

Figure 3:
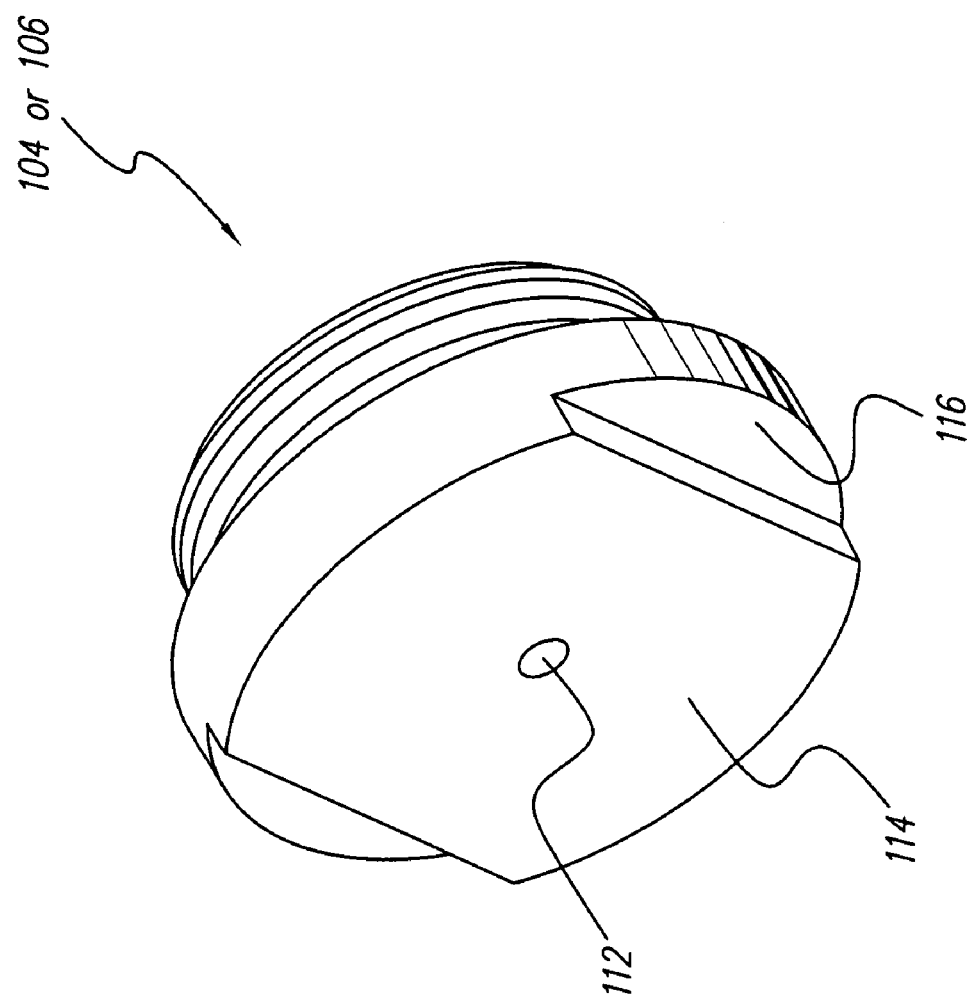
FIG. 3 is a schematic perspective view of one embodiment of an electrode of the microstimulator of FIG. 1.
Figure 4:
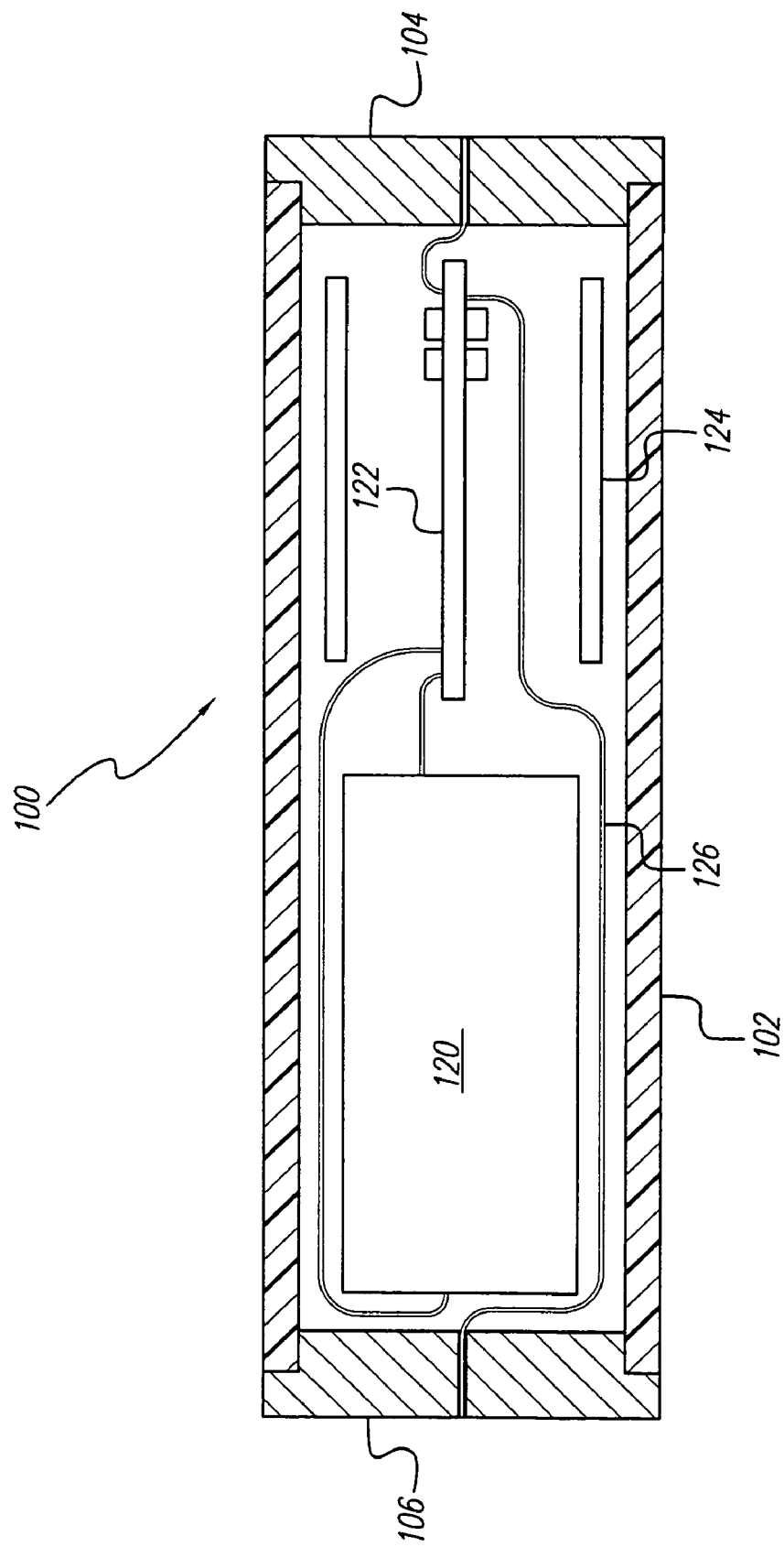
FIG. 4 is a cross-sectional view of one embodiment of a microstimulator, according to the invention.

As an alternative, the electrode 104 or 106 can include a hole 112 through the electrode body, as illustrated in FIG. 3. A lead 126 from the electronic subassembly 122 or power source 120 can then be guided through the hole and the lead can be attached to a conductive exterior surface 114 of the electrode. The attachment of the lead to the electrode can be performed by any method including, for example, soldering or laser welding. Generally, if a hole through the electrode body is utilized, the hole is also sealed prior to, simultaneously with, or after the attachment of the lead to the electrode surface to maintain a hermetically-sealed environment within the plastic housing. Other methods and arrangements for attaching a lead to each electrode can be used.

The arrangement with the lead extending through a hole in the electrode body can be particularly advantageous for manufacture because attachment of the lead to the exterior of the electrode is often easier than attaching the lead to the interior surface of the electrode. In addition, in some embodiments, the hole 112 allows air to pass out of the interior of the plastic housing as the electrode is attached so as to permit pressure equalization between the interior and exterior of the plastic housing during assembly of the microstimulator. Moreover, in at least some embodiments, prior to sealing one or both of the holes in electrodes 104, 106, the device can be heated to drive moisture from the interior of the plastic housing.

The electrodes 104, 106 may be positioned at ends of the plastic housing 102. In at least some embodiments, the electrodes 104, 106 are disposed at opposing or opposite ends of the plastic housing 102. For example, the electrodes 104, 106 can be disposed at opposite ends of a cylindrical plastic housing, as illustrated in FIG. 1.

The electrodes 104, 106 and plastic housing 102 may be coupled together to form a hermetically-sealed environment within the housing. In one embodiment, illustrated in FIGS. 2 and 3, the interior portions 108 of the ends of the plastic housing are threaded, as are the corresponding exterior surfaces 110 of the electrodes 104, 106, so that the electrodes can be screwed into the ends of the plastic housing. Optionally, an adhesive can be spread on either the interior portions 108 of the housing or the exterior surfaces 110 of the electrodes or both to further seal the plastic housing 102 and electrodes 104, 106. Preferably, the selected adhesive is moisture resistant and biocompatible.

Another option for enhancing the sealing of the electrodes to the plastic housing is to provide a solvent disposed on the surfaces 110 of one or both of the electrodes 104, 106 and capable of at least partially dissolving or deforming the plastic material of the plastic housing 102 so that the plastic housing is solvent welded or otherwise better adhered or conformed to the electrode(s).

As yet another option, the ends of the plastic housing can be heated, ultrasonically or otherwise, for sealing of the plastic housing to the electrodes. Heating may result in better conformation or bonding of the plastic housing to the electrodes. Moreover, in an embodiment in which the electrodes are formed using a plastic material with conductive overcoating, heating may result in mixing, if desired, of the plastics of the housing and electrodes to improve bonding.

Figure 2:
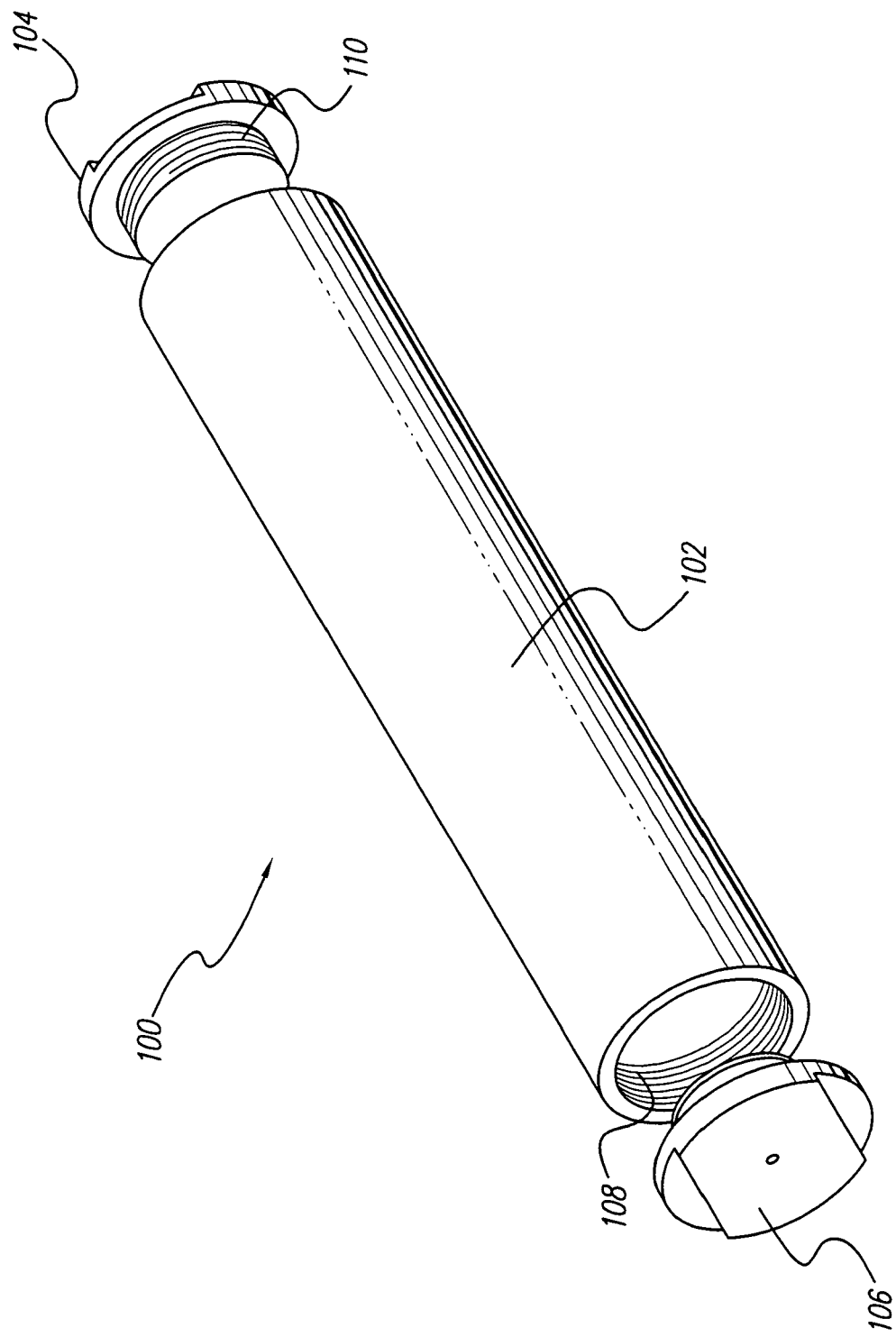
FIG. 2 is a schematic exterior perspective view of components of the microstimulator of FIG. 1.

FIGS. 1-3 also illustrate electrodes 104 or 106 with optional cut-out sections 116 that can facilitate pushing or screwing the electrode into the plastic housing by hand or with a tool that grips the electrode.

It will be understood that other methods of coupling the electrodes and plastic housing can be used. Such methods can include one or more of the following: adhesively attaching the electrodes to the housing; sliding at least a portion of the electrodes into the housing to form a compressive or frictional fit; screwing threaded interior surfaces of the electrodes onto threaded exterior surfaces of the plastic housing; coating a sealed end of the plastic housing (optionally with a hole extending through the housing for the lead) with a conductive material to form an electrode or the like.

In at least some embodiments, the length of the combined plastic housing 102 and electrodes 104, 106 is no greater than 30 mm. Typically the length of the combined plastic housing 102 and electrodes 104, 106 is in the range of 10 to 30 mm.

A power source 120 can be disposed within the plastic housing 100. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the microstimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 5) external to the user. Examples of such arrangements can be found in the microstimulator references identified above.

Figure 5:
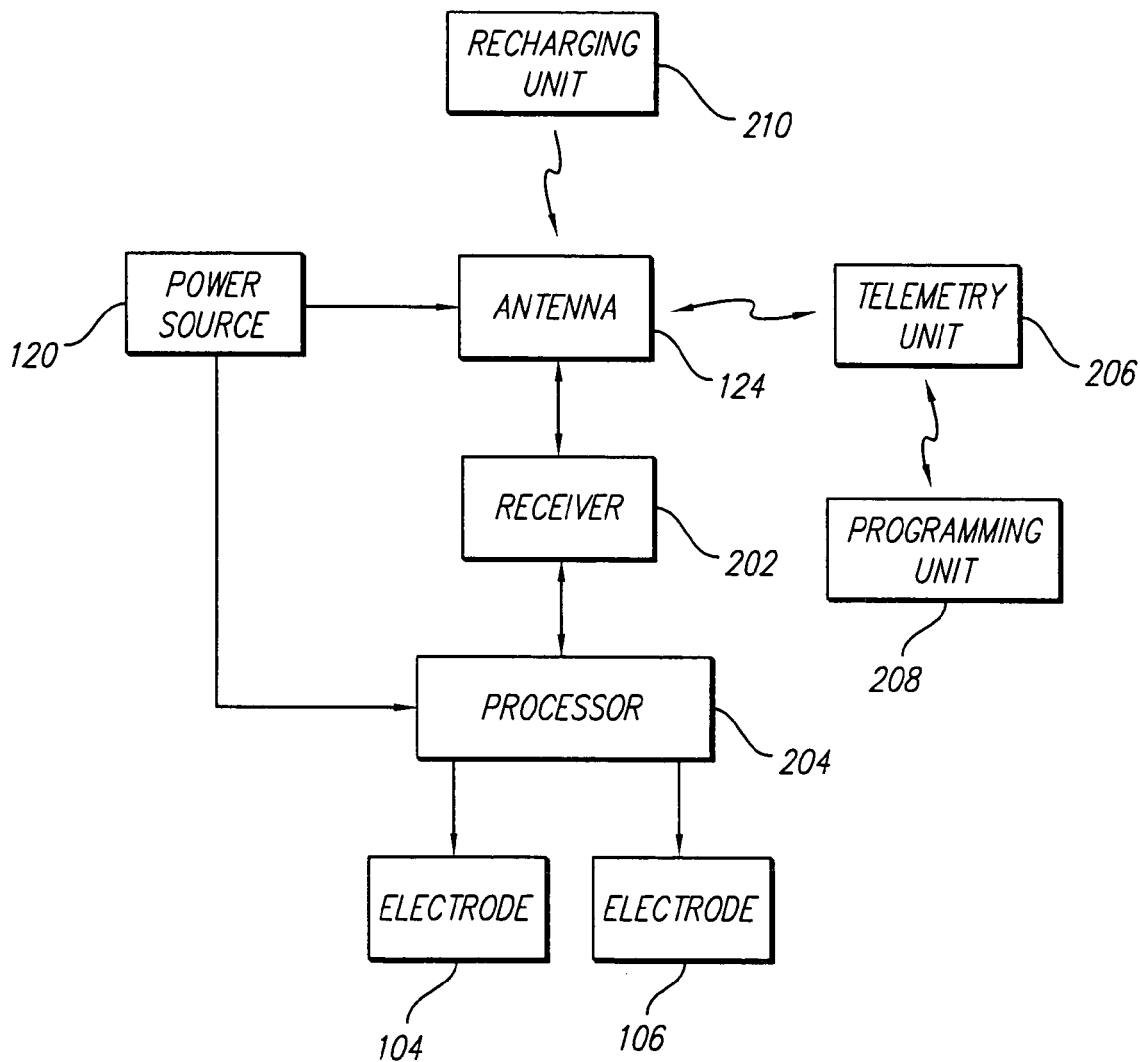
FIG. 5 is a schematic overview of components for a system for microstimulation of body tissues, according to the invention.

In one embodiment, electrical current is emitted by the electrodes 104, 106 to simulate motor nerve fibers, muscle fibers, or other body tissues near the microstimulator. The electronic subassembly 122 provides the electronics used to operate the microstimulator and generate the electrical pulses at the electrodes 104, 106 to produce stimulation of the body tissues. FIG. 5 illustrates one embodiment of components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the plastic housing, if desired.

In the illustrated embodiment, a processor 204 is provided to control the timing and electrical characteristics of the microstimulator. For example, the processor can, if desired, control one or more of the timing, periodicity, strength, duration, and waveform of the pulses. Any processor can be used and can be as simple as a electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted microstimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery. One advantage of a plastic housing is that plastic is typically more transparent to RF signals than metallic or ceramic materials. Thus, in some instances RF signals may be more reliably received or transmitted and received using less power or over longer distances.

Optionally, the microstimulator may include a transmitter (not shown) coupled to the processor and antenna for transmitting signals back to the telemetry unit 206 or another unit capable of receiving the signals. For example, the microstimulator may transmit signals indicating whether the microstimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within the plastic housing.

Any method of manufacture of the microstimulator can be used. For example, the electronic subassembly, power source, and antenna can be manufactured as described in U.S. Patent Application Publication No. 2004/0059392. These components can then be placed inside the plastic housing (or, alternatively, the plastic housing can be formed, e.g., molded, around the components). The electrodes can be attached to the plastic housing, for example, screwed into opposite ends of the housing, and leads from the electronic subassembly can be attached to the electrodes. Coatings on the electrodes or plastic housing, if any, can be applied at appropriate points during the manufacturing process.

The microstimulator can be implanted into the body tissue using a variety of methods including surgical methods. In some embodiments, the microstimulator can be implanted using a hypodermic needle or other insertion cannula. Examples of insertion techniques can be found in U.S. Pat. No. 6,051,017.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable microstimulator comprising:
    an elongate plastic housing having a first end and a second end, wherein the first end includes a first plastic threaded region and an access to an interior of the housing;
    an electronic subassembly disposed within the interior of the housing;
    a first end cap comprising a plastic body, a second plastic threaded region, and a conductive coating coated over at least a portion of the plastic body to form a first electrode, wherein the first electrode is in electrical communication with the electronic subassembly and the first and second plastic threaded regions are dimensioned to mate to form a seal between the first end and the first end cap and block the access to the interior of the housing, and wherein the first and second plastic threaded regions are solvent welded or melted directly to each other to facilitate a hermetic, plastic seal; and
    a second electrode disposed at the second end of the plastic housing and in electrical communication with the electronic subassembly;
    wherein the access is dimensioned to allow insertion of the electronic subassembly therethrough.

2. The implantable microstimulator of claim 1, further comprising a power source disposed within the plastic housing.

3. The implantable microstimulator of claim 1, further comprising a second end cap comprising the second electrode and a third threaded region.

4. The implantable microstimulator of claim 3, wherein the second end cap comprises:
    a plastic body, wherein the third threaded region is a third threaded plastic region; and
    a conductive coating coated over at least a portion of the plastic body, the conductive coating forming the second electrode.

5. The implantable micro stimulator of claim 1, wherein the plastic housing comprises a hydrophobic plastic.

6. The implantable microstimulator of claim 1, wherein plastic housing comprises polyolefins, polypropylene homopolymer or copolymer, TEFLON™, or polyetheretherketone.

7. The implantable microstimulator of claim 1, further comprising a coating disposed over the plastic housing.

8. The implantable microstimulator of claim 7, wherein the coating increases moisture resistance of the plastic housing.

9. The implantable microstimulator of claim 1, further comprising a solvent weld of a plastic material of the plastic body of the first end cap directly to a plastic material of the plastic housing.

10. The implantable microstimulator of claim 1, further comprising a melt seal of a plastic material of the plastic housing directly to a plastic material of the plastic body of the first end cap.

11. The implantable microstimulator of claim 1, wherein: the first electrode defines a hole through which a lead is disposed; and
the lead is coupled to the electronic subassembly and the first electrode.

12. The implantable microstimulator of claim 1, wherein:
the plastic housing is a cylinder; and
the first and second electrodes are disposed at opposite ends of the cylinder.

13. The implantable microstimulator of claim 1, wherein the first and second ends are opposing ends of the plastic housing.

14. The implantable microstimulator of claim 1, further comprising an antenna disposed within the plastic housing and coupled to the electronic subassembly.

15. The implantable microstimulator of claim 1, wherein the first end cap comprises a laterally-directed surface oriented to facilitate screwing of the first end cap into the plastic housing.

16. An apparatus comprising:
    an implantable microstimulator comprising
        an elongate plastic housing having a first plastic threaded region at a first open end and a second plastic threaded region at a second open end,
        an electronic subassembly disposed within the interior of the plastic housing, wherein the electronic subassembly is dimensioned to be insertable through at least one of the first open end and the second open end,
        a first end cap comprising a third plastic threaded region and a first electrode, wherein the first electrode is in electrical communication with the electronic subassembly and the first and third plastic threaded regions are dimensioned to mate to cap the first open end and block fluid access to the interior of the housing when the implantable microstimulator is implanted in a patient, and
        a second end cap comprising a fourth plastic threaded region and a second electrode, wherein the second electrode is in electrical communication with the electronic subassembly and the second and fourth plastic threaded regions are dimensioned to mate to cap the second open end and block fluid access to the interior of the housing when the implantable microstimulator is implanted in a patient.

17. The apparatus of claim 16, further comprising an external control unit configured and arranged to communicate with the electronic subassembly to provide signals to the implantable microstimulator, wherein the external control unit comprises a programming unit comprising an interface for entering information to be provided to the microstimulator.

18. The apparatus of claim 16, further comprising an external control unit configured and arranged to communicate with the electronic subassembly to provide signals to the implantable microstimulator, wherein the external control unit comprises a telemetry unit with a transmitter to transmit the signals to the implantable microstimulator.

19. An implantable microstimulator comprising:
    an elongate plastic housing having a first end and a second end, wherein the first end includes a first plastic threaded region and an access to an interior of the housing;
    an electronic subassembly disposed within the interior of the housing;
    a first end cap comprising a second plastic threaded region and a first electrode, wherein the first electrode is in electrical communication with the electronic subassembly and the first and second plastic threaded regions are dimensioned to mate to form a seal between the first end and the first end cap and block fluid access to the interior of the housing when the microstimulator is implanted in a body of a patient; and a second electrode disposed at the second end of the plastic housing and in electrical communication with the electronic subassembly;

wherein the access is dimensioned to allow insertion of the electronic subassembly therethrough.

* * * * *